United States Patent [19]

Bunnelle et al.

[11] Patent Number: 4,543,099

[45] Date of Patent: * Sep. 24, 1985

[54] METHOD FOR IMPARTING ELASTIC PROPERTIES TO A FLEXIBLE SUBSTRATE

[75] Inventors: William L. Bunnelle, Stillwater; Richard C. Lindmark, Jr., Coon Rapids, both of Minn.

[73] Assignee: H. B. Fuller Company, Saint Paul, Minn.

[*] Notice: The portion of the term of this patent subsequent to Nov. 29, 2000 has been disclaimed.

[21] Appl. No.: 399,780

[22] Filed: Jul. 19, 1982

Related U.S. Application Data

[62] Division of Ser. No. 247,998, Mar. 26, 1981.

[51] Int. Cl.⁴ .................. B32B 27/08; B32B 31/08
[52] U.S. Cl. ............................ 604/385 A; 2/401;
 156/164; 156/183; 156/229; 156/231;
 156/244.11; 156/244.23; 156/244.24; 156/269;
 156/324; 156/334; 428/152; 428/517; 428/906;
 525/97; 525/98
[58] Field of Search .......... 156/243, 244.11, 244.23,
 156/244.24, 210, 229, 164, 183, 231, 269, 324,
 334; 2/401; 525/97, 98; 428/152, 517, 906;
 604/385

[56] References Cited

U.S. PATENT DOCUMENTS

| T975,004 | 10/1978 | Hansen et al. | 525/98 |
|---|---|---|---|
| 3,600,250 | 8/1971 | Evans | 156/244.24 |
| 3,641,205 | 2/1972 | La Flair et al. | 525/97 |
| 3,956,223 | 5/1976 | Chiang et al. | 525/97 |
| 4,046,838 | 9/1977 | Feeney | 525/97 |
| 4,259,220 | 3/1981 | Bunnelle et al. | 525/98 |
| 4,418,123 | 11/1983 | Bunnelle et al. | 156/244.11 |

Primary Examiner—Caleb Weston
Attorney, Agent, or Firm—Merchant, Gould, Smith, Edell, Welter & Schmidt

[57] ABSTRACT

A purpose of the disclosed method is to impart gathers and elasticity to a relatively inelastic film, membrane, or web substrate, through elastic banding with a viscoelastic hot melt pressure-sensitive adhesive (PSA). Typically, the resulting elastic-banded substrate product (e.g. 40) will be cut into discrete units and formed in to garments or body-encircling members such as disposable diapers. One step of the preferred method involves extruding a ribbon or band (13 or 113) comprising a viscoelastic hot melt PSA, which PSA has unusually high cohesion, stretchiness, and elasticity without excessive loss of adhesive bonding strength. (The viscoelastic behavior of the PSA is believed to be determined, at least in part, by the relative size of its crystalline domains and its rubbery domains and the glass transition temperatures and softening point of its components.) A second step of the preferred method involves bringing the band of hot melt (13 or 113) into adherent contact with a surface of a moving continuous substrate (22 or 32 or 132). A typical substrate would be the polyolefin film used in the manufacture of disposable diapers. The band can be bonded to the substrate through a pressure activation technique, wherein the band itself has the necessary inherent adhesive properties.

23 Claims, 2 Drawing Figures

METHOD FOR IMPARTING ELASTIC PROPERTIES TO A FLEXIBLE SUBSTRATE

This is a division of application Ser. No. 247,998, filed Mar. 26, 1981.

TECHNICAL FIELD

This invention relates to a method for imparting elastic characteristics to materials which are relatively inelastic through the use of a hot melt pressure-sensitive adhesive. An aspect of this invention relates to the formulation of a suitable hot melt pressure-sensitive adhesive composition for the aforementioned method. Still another aspect of this invention relates to the manufacture of garments or body-encircling members provided with an elastic band. Additional aspects of the invention relate to the elastic banding of such garments or body-encircling members which are cut from a continuously moving film, membrane, or web-like substrate and hot melt pressure-sensitive compositions employed in the elastic banding process which compositions can take the form of extrudates, and elastic banding of discrete articles wherein the hot melt pressure-sensitive adhesive composition can be in the form of a tape.

DESCRIPTION OF THE PRIOR ART

In the garment industry, vulcanized rubber in sheet or thread form is typically used for elastic banding purposes. Traditionally, the vulcanized rubber has been sewn, woven, or bonded to the garment or discrete unit of material. Crosslinked synthetic rubbers can be used in place of vulcanized natural rubber for this purpose.

Sewing or weaving or similar attachment techniques are not well suited to modern, high-production processes and may even be inconvenient or cumbersome to use in making homemade garments. A more efficient technique for attaching an elastic band involves the use of a heat-activated coating on the elastic or a separate adhesive, which adhesive can be coextensive in length with the elastic or merely applied in spots. Taking his cue from this more efficient approach, the patentee of U.S. Pat. No. 4,081,301 (Buell), issued Mar. 28, 1978 developed a high-production process particularly well suited to providing disposable diapers with elastic leg bands. According to the Buell patent, glue applicators can apply adhesive along the length of continuous bands of elastic which are applied, in a stretched condition, to the continuous web from which the disposable diapers are made. The patent further suggests that the elastic band or ribbon can be coated with a heat-activated adhesive prior to contact with the web. Still another suggestion relates to the use of a heat-sealable elastic ribbon which can be adhered to the web with the aid of a suitable heating means.

Still greater efficiency (with a concurrent simplification of the overall elastic banding process) could theroetically be provided if the adhesion of the elastic band to the substrate did not require either a separate adhesive or a heating means. Unfortunately, there are few guidelines in the prior art for one who would attempt to formulate an adhesive which could itself be an elastic band. It is known that "pressure-sensitive" adhesives do not require heat, solvents, moisture, or the like to form a reasonably strong adhesive bond under normal ambient conditions. It is also known that such adhesives possess a degree of stretchiness, cohesion, and elasticity as well as adhesion characteristics. However, the four-fold balance of adhesion, cohesion, stretchiness, and elasticity is a delicate one, and any substantial increases in the last three of these properties can result in unacceptable losses of adhesion.

Since the invention of pressure-sensitive adhesives, literally decades of research effort have gone into the investigation of the aforementioned four-fold balance and the development of tests for reproducibly measuring the desired properties. For example, the adhesive bond strength of a pressure-sensitive adhesive can be measured by 180° peel resistance tests such as PSTC-1. The adhesive tack can be measured, for example, by probe tack tests such as A.S.T.M. D2979. Cohesion and stretchiness of adhesives can be measured with modern tensile testing equipment.

A particularly unusual problem may be encountered when the adhesive is in a temperature environment which is continuously above normal ambient or room temperature. It has been found that some pressure-sensitive adhesives have their four-fold balance significantly altered when the environment is characterized by a modestly elevated temperature. This finding is of great importance in the case of garments or body-encircling members which are continuously exposed to body temperature (e.g. 37° C.).

Most modern pressure-sensitive adhesives ("PSA's") are applied to a substrate by one of three techniques: coating from an organic-solvent based solution (e.g. solvent casting), coating from a suspension or dispersion such as an aqueous latex, and coating or extruding of a hot melt pressure-sensitive composition. The hot melt technique has a number of advantages; for example, thicker layers of adhesive are readily obtainable, solvent recovery is unnecessary, and drying or "setting" time is minimal or nonexistent. Research activity in the field of hot melt pressure-sensitive adhesives has been very extensive, and even a respresentative citation of references drawn from this field would be difficult to provide. The following selection of patents and literature is believed to be reasonably representative.

| U.S. Pat. No. | Patentee | Issue Date |
| --- | --- | --- |
| 3,686,107 | Russell | August 22, 1972 |
| 3,736,281 | Russell | May 29, 1973 |
| 3,827,999 | Crossland | August 6, 1974 |
| 3,935,338 | Robertson et al | January 27, 1976 |
| 3,954,692 | Downey | May 4, 1976 |
| 4,089,824 | Bronstert et al | May 16, 1978 |
| British Patent | Inventor | Publication Date |
| 1,405,786 | Crossland | September 10, 1975 |

*Kirk-Othmer Encyclopedia of Chemical Technology,* 2nd Edition, Volume 1, John Wiley & Sons, Inc., New York; N.Y., 1963, pages 381–384.

"SOLPRENE ®418 in Pressure Sensitive Adhesives", Bulletin 304 of Phillips Chemical Co., a division of Phillips Petroleum Company.

SUMMARY OF THE INVENTION

It has now been found that a greatly simplified method for imparting elasticity to a relatively inelastic substrate can be provided if one extrudes a band comprising a suitable viscoelastic hot melt pressure-sensitive adhesive, cools the thus-extruded band to a temperature below its softening point but above its glass transition temperature, and brings the thus-cooled band into contact with the substrate to form a pressure-sensitive adhesive (PSA) bond, typically by means of pressure only, although modest amounts of heat can be used also, if desired. The band of hot melt can be pre-extruded and formed into a convoluted roll of hot melt pressure-sensitive adhesive tape. If the pre-extruded technique is used, a cooling step is ordinarily unnecessary, since the roll will ordinarily be stored and unreeled at ordinary ambient temperatures. Extruding the band of hot melt pressure-sensitive adhesive is by far the most practical approach when applying the elastic band to a continuous non-elastomeric film, membrane, or web substrate which is subsequently cut into portions suitable for use as elastic-banded articles. The convoluted tape approach is very practical when a length of tape is to be applied to an individual article.

In the context of this invention, a suitable hot melt pressure-sensitive adhesive will have viscoelastic behavior because of its glass transition and/or softening point characteristics and particularly because of a microstructure comprising the combination of crystalline domains with rubbery domains. The crystalline domains contribute a pseudo-crosslinked character and greater elasticity and cohesion. High elasticity and elastomeric behavior are typically manifested by a storage modulus ($G'$) which is higher, and a loss tangent (tan $\delta$ or $G''/G'$) which is lower, than most conventional PSA's. However, the storage modulus values cannot be so high as to preclude viscoelastic behavior in the temperature range of 25°–50° C. A viscoelastic solid, under stress, has some of the properties of a highly viscous liquid (e.g. "creep" or "cold flow") as well as some of the properties of an elastomer. A PSA with suitable "creep" or "cold flow" properties will have some tendency to flow in the temperature range of 25°–50° C., but this tendency should be kept within limits, as manifested by a limited range of loss modulus ($G''$) values.

The following are considered to be illustrative values for the $G''$, $G'$, and tan $\delta$ (tan $\delta = G''/G'$) of a suitable PSA.

| Property | Values at 25–50° C. and 0.01–0.25 Hz |
|---|---|
| Loss Modulus ($G''$) | $4 \times 10^4$ to $35 \times 10^4$ dynes/cm$^2$ |
| Storage Modulus ($G'$) | $75 \times 10^4$ to $200 \times 10^4$ dynes/cm$^2$ |
| Loss Tangent | 0.03 to 0.3 |

To provide sufficiently large crystalline domains, the PSA preferably contains either a rubbery block copolymer with large vinyl arene (e.g. polystyrene) end blocks or an aromatic, essentially hydrocarbon resin associated with these end blocks. Some frequency-dependence of these values can be observed, but extreme temperature dependence is not desirable. For example, a loss of more than $50 \times 10^4$ dynes/cm$^2$ in $G'$ at 50° C., as compared to 25° C. indicates the likelihood of "heat set" or inadequate elastomeric behavior at moderately elevated temperatures. Permanent deformation due to elongation should not exceed about 1.5 times the original length of a sample of the PSA (i.e. a permanent increase in length equal to 50% of the original length) throughout the 25°–50° C. range, using the dead load creep test described subsequently.

Figure 1:
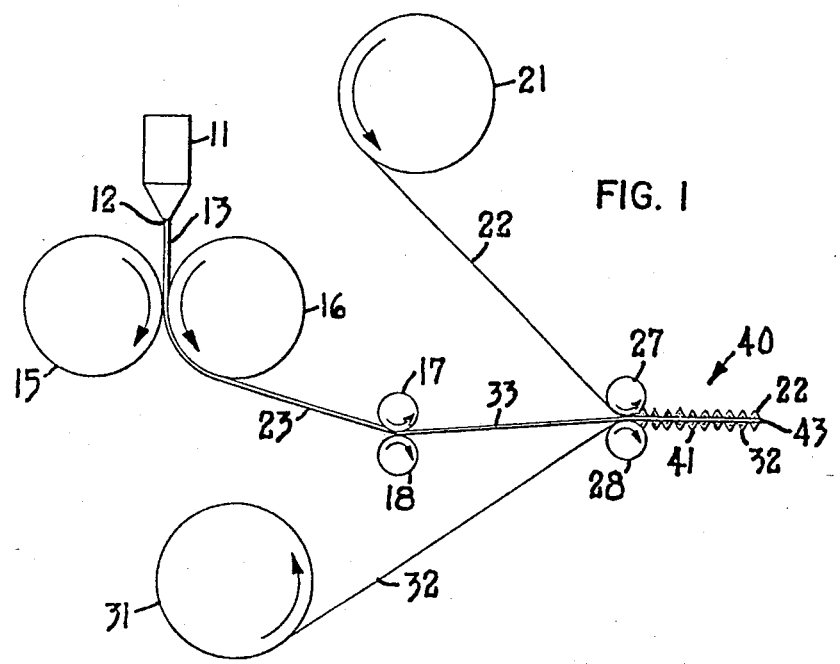
FIG. 1 is a schematic illustration fo a typical apparatus and typical method steps used in a preferred embodiment of this invention.

When used in this application, the following terms have the indicated meanings.

"Pressure-sensitive adhesive" denotes those adhesives which bond almost instantaneously when contact pressure is applied to force the mating surfaces together. Such adhesives have rather high cohesive strength, such that, if the adhesive is peeled away from a smooth surface to which it has adhered, no apparent offsetting occurs and no appreciable residue remains on the smooth surface. True pressure-sensitive adhesives (PSA's) need not be in a liquid or molten state in order to have adhesive properties. Similarly, moisture, solvents, heat, or the like are not needed to activate a PSA. Some PSA's have aggressive tack or "quick stick" at room temperature and tend to bond instantly upon contact. The PSA's of this invention, on the other hand, typically require light pressure to form a bond of appreciable strength. In other words, the tack is relatively non-aggressive and ordinarily would not be sensed until some pressure were applied to the surface of the PSA, causing it to "cold flow" in the manner of most viscoelastic materials. Thus, a PSA of this invention has a rheology which permits sufficient flow under pressure to form a strong adhesive bond while nevertheless maintaining a high level of cohesion, stretchiness, and elasticity.

"Hot melt" refers to thermoplastic solids with reasonably stable properties in the molten state, which are easily melted at modestly elevated temperatures (e.g. temperatures above 65° C.) and/or easily extruded, and which can be melted and resolidified a number of times without excessive degradation of the thermoplastic properties. A "hot melt pressure-sensitive adhesive" or "hot melt PSA" refers to a hot melt adhesive having PSA characteristics at temperatures below the softening point and above the glass transition temperature of the hot melt.

"Softening point" refers to a specific temperature or range of temperatures which can be determined by any of the standard softening point tests such as the ring and ball ("R & B") test. Accordingly, the term "softening point" includes and subsumes "softening range".

"Elastomer" and "elastomeric" refer to a material which, in the form of an unsupported film or layer can be elongated to at least 100% of its original length and which will return with force to substantially its original length when permitted to contract spontaneously. Thus, this invention contemplates as "elastomers" those materials which would be defined as "elastomeric" by the American Society for Testing and Materials (A.S.T.M.). "Non-elastomeric" materials are those which exhibit some degree of significant deformation or "set" when elongated 100% of their original length or less; that is, such non-elastomeric materials typically do not provide the elongation-resistant forces of an elastomer.

"Essentially hydrocarbon resin" refers to a resin in the molecular weight range of a few hundred up to several thousand (e.g. 8,000) which is obtained or synthesized from rather basic hydrocarbonaceous materials such as petroleum, coal tar, turpentine, olefins and other unsaturated simple hydrocarbons, and the like. In the context of this invention, an "essentially hydrocarbon resin" need not be a hydrocarbon in the strictest sense of the term and may contain oxygen, nitrogen, or sulfur, e.g. as hetero-atoms or as atoms of functional groups.

Thus, an "essentially hydrocarbon resin" can be made from a monomer such as coumarone (also known as benzofuran). And, in industrial practice, coumarone-indene resins are typically referred to as "hydrocarbon resins".

The terms "loss tangent" (tan δ or G''/G'), "storage modulus (G')", "loss compliance (J'')" and "storage compliance" (J') are defined according to established principles of dynamic mechanics. These rheological quantities are measured on samples approximately 2.5 mm in thickness placed between 25 cm parallel plate fixtures of a Rheometrics Mechanical Spectrometer (RMS). The sample was allowed to equilibrate with the test temperature (e.g. 25° C. or 50° C.). A minicomputer accurately governs the application of a 5% peak-to-peak shear strain to the sample. The frequency of the application can be accurately controlled to a fraction of a Hertz (Hz). The values of the complex modulus (G*) and loss tangent are calculated by the computer from geometry factors, peak-to-peak amplitude of the torque signal, and phase lag of the torque output wave. The definition of loss tangent and the relationship between G*, G', and G'' provide two equations in two unknowns which can be solved by the computer to provide G'' and G', since G* and loss tangent are both known values calculated as described previously. The value for J' is given by the reciprocal of G' divided by the expression $1 + \tan^2 \delta$; the value of J'' is given by the reciprocal of G'' divided by $1 + (\tan^2 \delta)^{-1}$. For any of these values, the frequency in Hz (e.g. 0.25 Hz or 0.01 Hz) must be specified. Other instruments for measuring these rheological properties over a range of frequencies are known, e.g. the "RHEOVIBRON".

The term "dead load deformation" or "dead load creep" refers to a measurement of "cold flow" or permanent deformation at one or more fixed test temperatures, e.g. 23° C. or 25° C., 40° or 41° C., and 49° or 50° C. A sample of known length is suspended vertically in a chamber maintained at the test temperature and a weight (e.g. 1500 grams) is attached to the lower (free) end of the sample. The sample is cut to a size such that the force per unit area is 1500 g/cm². After approximately 3 hours at the test temperature, the sample is removed, the weight is detached, and the sample is allowed to relax under the influence of its own inherent elastomeric forces. The length of the relaxed sample ($L_2$) is compared to the original length ($L_1$) and the "dead load creep" (permanent deformation) is determined according to the formula $(L_2 - L_1)/L_1 \times 100\%$.

Turning now to the Drawing, FIG. 1 illustrates the use of a pre-tensioned, cooled band of hot melt PSA to bond two continuous substrates into an assembly having gathers all along the bond line. A hot melt reservoir 11 extrudes an elongated extrudate (referred to herein as a "band") by forcing the hot melt PSA material in reservoir 11 through an extrusion die 12. The hot melt PSA band 13 comes into contact with chill rolls 15 and 16 almost immediately after the extrusion step, so that band 13 will be cooled to a temperature below its softening point, e.g. to a normal ambient temperature such as 20°–25° C. (Typically, the hot melt PSA will be formulated to have a glass transition temperature below normal ambient temperatures). Chill rolls 15 and 16, in addition to cooling band 13, also advance it toward tensioning rolls 17 and 18. Accordingly, the portions 23 and 33 of band 13 which are on either side of tensioning rolls 17 and 18 will be under tension and will be in an essentially elongated state. Tensioning rolls 17 and 18 advance portion 33 of band 13 to nip rolls 27 and 28. Substrates 22 and 32 are all the while being continuously unreeled from storage rolls 21 and 31, so that the pretensioned, cooled band of hot melt PSA 33 and substrates 22 and 32 all enter the nip provided by rolls 27 and 28 to be formed into the composite or assembled product 40 (i.e. the banded substrates). Although nip rolls 27 and 28 can be heated to a moderately elevated temperature, in the preferred embodiment of this invention, the modest pressure provided by the nip rolls is all that is needed to adhesively bond substrate 22 to substrate 32 with the hot melt PSA band 33. Since the nip rolls 27 and 28 provide only line contact with the composite or assembly comprising substrate 22 and 32 and adhesive 33, it is difficult to express the pressure applied by these rolls in conventional terms such as Kg/m² or the like. Light pressure on the order of tens or hundreds of grams per square centimeter can be sufficient; however, there is almost no upper limit on the pressure applied by nip rolls 27 and 28 so long as the rolls themselves or the substrates 22 and 32 are not damaged. The hot melt PSA in band 13 can be formulated to take into account the amount of pressure available at nip rolls 27 and 28.

Since band 13 is a viscoelastic hot melt PSA which meets the definition of an elastomer, it will tend to contract spontaneously with force if the tension applied to banded substrates 40 is less than the tension on portion 33 of band 13. For example, additional rolls or conveying devices (not shown) can be used on banded substrates 40 merely to move the composite product along toward a cutting station and not exert any significant tension upon the banded substrates. In such a situation, the portion 43 of band 13 on the exit side of nip rolls 27 and 28 will spontaneously cause the formation of gathers 41 all along the line of the adhesive bond between band 43 and substrates 22 and 32.

The banded substrate product 40 can be cut into individual elastic-banded articles such as disposable diapers by techniques known in the art.

Figure 2:
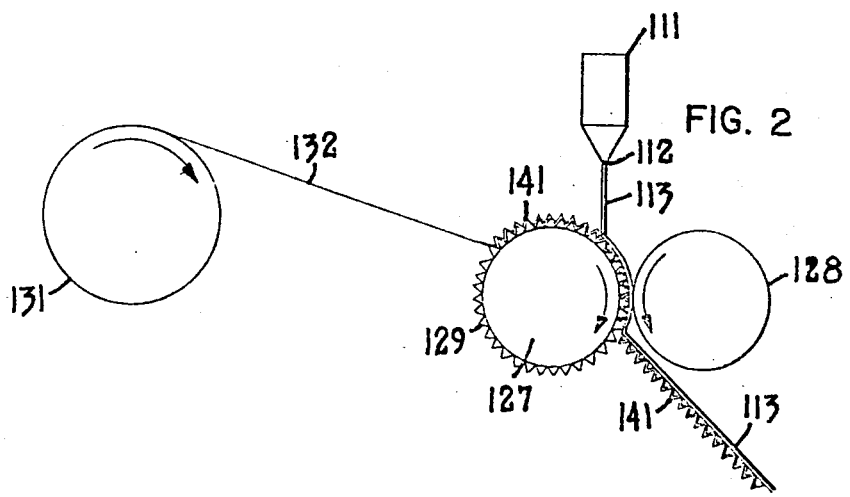
FIG. 2 is a similar schematic illustration of another embodiment of this invention.

In the embodiment of the invention shown in FIG. 2, pre-tensioning of the hot melt PSA band 113 is not required. As in FIG. 1, band 113 is extruded from reservoir 111 through extrusion die 112. A single substrate 132 is continuously unreeled from storage roll 131. Substrate 132 is taken up by vacuum chill roll 127 at a point which permits pre-gathering of the substrate. Teeth-like projections 129 on the surface of vacuum chill roll 127 create the flutes or gathers 141 in substrate 132. The two chill rolls 127 and 128 serve to cool band 113 in a manner analogous to the action of chill rolls 15 and 16 of FIG. 1; in addition, these chill rolls apply light pressure to the composite of the band 113 and the pre-gathered substrate 132, so that the pressure-sensitive adhesive bond between band 113 and substrate 132 is formed without permanently flattening out gathers 141. This result occurs because, in the composite emerging from the exit side of rolls 127 and 128, band 113 tends to be bonded only to the peaks of gathers 141.

The foregoing methods are particularly well suited to high-volume production techniques using continuous substrates. For low-volume or batch production, the elongation-resistant gathers can be imparted to portions of the substrate by means of a pressure-sensitive adhesive tape. In this technique, the desired length of tape is simply unreeled from a convoluted roll of hot melt pressure-sensitive adhesive, which adhesive has been applied to a flexible continuous backing. For good results in this technique, the pressure-sensitive adhesive tape should have an extruded layer at least 50 micrometers ($\mu$M) in thickness, more typically at least 75 or 100 $\mu$M in thickness. If the flexible continuous backing is relatively inelastic as compared to the hot melt PSA layer of the tape, the backing should have release characteristics, so that it can be delaminated from the tape structure in the manner of a transfer tape. The cohesive, self-supporting PSA layer removed from the tape can be elongated and applied to, for example, a garment in the stretched condition. Gathers will be introduced into the garment all along the lines of the adhesive bond after pressure-sensitive bonding has been completed. A modest amount of pressure can be applied by machine or by hand to insure a strong adhesive bond. A non-sticking coated roller or the like can be used to apply the pressure, particularly superior non-stick properties being obtained with fluoropolymer or, less preferably, silicone coatings.

Delamination of the tape is not necessary if the backing of the pressure-sensitive adhesive tape is itself highly elastomeric. Such a tape structure can be provided, for example, by coextruding the backing and the PSA through a single extrusion die. The resulting stretchy tape can be rolled upon itself or convoluted, particularly if the exposed side of the elastomeric backing is treated so as to be essentially non-sticky. Special sizings and the like which prevent the formation of a PSA bond are known in the art and can be employed for this purpose.

Viscoelastic hot melt pressure-sensitive adhesives (PSA's) of this invention preferably comprise a rubbery block copolymer and at least two different types of resins which associate with different parts of the rubbery block copolymer molecule. The resin which associates with the crystalline vinyl arene end blocks of the block copolymer tends to increase the size of these crystalline domains, thereby, it is believed, decreasing the temperature dependence of the elastic aspect of the viscoelastic behavior of the PSA. (However, this invention is not bound by any theory.) The adhesive character of the PSA is believed to be dependent in part upon the high-viscosity liquid character of the PSA within the 25°–50° C. temperature range. A characteristic of a viscous liquid is that it will yield to stress, and at least some strain (in an oscillating stress situation) will be up to 90° out of phase with the stress. By contrast, in a perfectly elastic solid the stress and strain would always be in phase. The previously given broad ranges of G'', G', and loss tangent (and particularly the preferred and optimum ranges given subsequently) are believed to indicate a highly effective balance of viscoelastic properties in the 25°–50° C. range, whereby at least some elasticity is provided (note the loss tangent $<1$ and the G' of $65\times 10^4$ dynes/cm$^2$ or more), but in combination with some ability to flow or "wet out" a substrate (note the loss tangent $>0.03$, the G'$<200\times 10^4$ dynes/cm$^2$, and G''$<100\times 10^4$ dynes/cm$^2$), without resulting in a viscosity so low as to permit excessive "creep" or cold flow (not the G''$>3\times 10^4$).

Although this invention is not bound by any theory, it is believed that enlargement of crystalline or vinyl arene domains will increase the storage modulus (G') and decrease the dead load creep, but some PSA behavior (e.g. peel strength) may be lost. Conversely, enlargement of midblock domains and/or increased tackifying of these domains may increase PSA behavior but also increase dead load creep and excessively decrease loss modulus (G'') and storage modulus (G') data. The ideal PSA for this invention appears to provide a balance of high-viscosity liquid and elastic solid behavior, resulting in low dead load creep, good PSA properties, and properly balanced rheological data. The G',G'', loss tangent, J' and J'' data can be considered to be "parameters" of the ultimate properties of dead load creep and PSA characteristics.

A tackifying resin with aliphatic character and relatively minimal aromatic character can associate with the midblock of the block copolymer and, if properly selected, help provide this viscoelastic balance in hot melt PSA behavior. Thus, a suitable viscoelastic hot melt PSA will typically comprise:

(1) a rubbery block copolymer which includes a rubbery midblock portion and which is terminated with crystalline vinyl arene blocks, (2) a tackifying resin generally compatible with and generally associated with the midblock portion of the block copolymer, and (3) an aromatic, essentially hydrocarbon resin having a glass transition temperature and a softening point above those of the tackifying resin and the end blocks of the block copolymer, which aromatic resin is generally compatible with and generally associated with the aforementioned end-blocks. This third component can be less than 10 wt.-% of the PSA if the block copolymer level is at least 45 wt.-%. This third component can be eliminated if the PSA comprises a major amount of rubbery block copolymer having a high end block content (e.g. 16–30% by weight of the copolymer). Levels of block copolymer higher than 75 wt.-% are difficult to tackify, however.

The hot melt pressure-sensitive adhesive will typically have a ball and ring softening point within the range of 65° to 240° C. It will exhibit elastomeric behavior above its glass transition temperature and particularly for extended periods at body temperature (e.g. 37° C.).

In addition to the block copolymer and resins, the hot melt PSA can contain the usual antioxidants or stabilizers and essentially inert ingredients which do not have a significant effect upon the properties of the combination of the rubbery block copolymer and the resins. For example, minor amounts of fillers and pigments can be included in the hot melt PSA, typically in amounts less than 5% by weight of the total hot melt PSA composition. Substantially inert extenders can also be included in the composition, e.g. the typical hydrocarbon process oils. The amount of process oil will typically also be kept below 5 weight-% of the composition, since large amounts of oil can detract from the elastic recovery characteristics of the PSA.

Typical antioxidants useful in PSA's of this invention include the pentaerithritol phosphite ester type (e.g. di[stearyl]pentaerithritol disphosphite), the hindered phenol or polyphenol type, and the like. Typical hindered phenol-type antioxidants include those in which a phenolic (i.e. hydroxyphenyl or hydroxybenzyl) group or groups is or are substituted on a short hydrocarbon chain, and the hydroxy group of the phenolic substituent is hindered by nearby or adjacent alkyl groups substituted on the phenol nucleus. Such structures can be obtained, for example, by alkylating or styrenating hydroxyphenyl compounds such as phenols and cresols.

Typical pigments useful in formulating PSA's of this invention include titanium dioxide, typically having a particle size in the sub-micrometer range, and similar finely divided materials. Fillers may tend to be a bit coarser in particle size, though still typically smaller than 40 μM (minus 325 U.S. mesh), e.g. finely ground calcium salts or silicates.

The following description of the preferred ingredients of hot melt PSA's of this invention will concentrate on the block copolymers and the resins.

A number of rubbery block copolymers can be tackified to produce hot melt PSA compositions, as can be seen from the disclosures in the aforementioned U.S. Pat. Nos. 3,686,107, 3,736,281, 3,827,999, 3,935,338, 3,954,692, and 4,089,824. Additional disclosures of this type can be found in British Pat. No. 1,405,786 and trade literature of Phillips Petroleum Company and Shell Chemical Company. The block copolymers used in this invention are rubbery, i.e. elastomeric. Though these copolymers are thermoplastic in the sense that they can be melted, formed, and resolidified several times with little or no change in physical properties (assuming a minimum of oxidative degradation), they exhibit some of the characteristics of cross-linked or vulcanized rubber. The apparent cross-linked character is provided by the aforementioned crystalline domains provided by vinyl arene terminal blocks or end blocks. The block copolymers also include a rubbery midblock portion which can be either linear or branched. In typical examples of a branched midblock, the midblock portion contains at least three branches which can be radiating out from a central hub or can be otherwise coupled together.

One way of synthesizing such rubbery block copolymers is to begin with the polymerization of the vinyl arene blocks which provide the end blocks. Once the vinyl arene blocks have been formed, they can be linked to elastomeric blocks, which elastomeric blocks are typically obtained by polymerizing unsaturated hydrocarbons, e.g. dienes such as butadiene, isoprene, and dienes of higher hydrocarbons. When an end block A is joined to an elastomer block B, an A-B block copolymer unit is formed, which unit can be coupled by various techniques or with various coupling agents to provide a structure such as A-B-A, which may in reality be two A-B blocks joined together in a tail/tail arrangement. By a similar technique, a radial block copolymer can be formed having the formula $(A-B)_nX$, wherein X is the hub or central, polyfunctional coupling agent and n is a number greater than 2. (If n were 2, the polymer would be A-B-X-B-A, which is equivalent to the A-B-A structure described previously and is essentially linear.) Using the coupling agent technique, the functionality of X determines the number of A-B branches.

Preferably, each block A has an average molecular weight between 1,000 and 60,000, and each block B has an average molecular weight between 5,000 and 450,000. The total molecular weight of the block copolymer is preferably in excess of 100,000 or 200,000, e.g. 300,000. An extensive discussion of rubbery radial block copolymers can be found in the disclosure of the aforementioned U.S. Pat. No. 4,089,824. As pointed out by the '824 patent, the residual unsaturation in the midblock or diene-containing portion of the block copolymer molecule can be hydrogenated selectively so that the content of olefinic double bonds in the radial block copolymers can be reduced to a residual proportion of less than 5% or even less than 2%. Such hydrogenation tends to reduce sensitivity to oxidative degradation and may have beneficial effects upon elastomeric properties.

Preferred block copolymers used in this invention have styrene and blocks and an isoprene midblock portion. The isoprene typically comprises the major amount of the repeating units in the copolymer and can constitute, for example, 70% by weight or more of the copolymer molecule. The midblock, if branched, can have three or more branches, and good results can be obtained with, for example, four, five, or six branches. The midblock can be hydrogenated, if desired.

Linear or A-B-A type block copolymers (including A-B-A-B-A, etc.) are preferably selected on the basis of end block content, large end blocks being preferred. For S-I-S (styrene-isoprene-styrene) block copolymers, a styrene content in excess of 15% by weight is preferred, e.g. 16–30% by weight. A commercially available example of such a linear polymer is KRATON ® 1111 rubber, an S-I-S polymer which contains about 21.5% styrene units, essentially the balance being isoprene units. Thus, the optimum styrene content for linear S-I-S copolymers appears to be greater than 20% by weight. As a result of the higher styrene content, the polystyrene end blocks have a relatively high molecular weight. Typical properties of KRATON ® 1111 are reported to include a tensile strength of 2900 psi ($2.0 \times 10^4$ kPa), a 300% modulus of 200 psi 1400 kPa), an elongation of 1200% at break, a 10% set at break, and a Shore A hardness of 52; the Brookfield viscosity of a toluene solution is 1300 centipoise at room temperature, less than that of KRATON ® 1107.

A variety of resins with tackifying properties are compatible with polymerized diene polymer blocks, including those diene blocks which have been hydrogenated so as to become virtually identical, chemically and physically, to polymerized mono-olefins (e.g. polyethylene, polypropylene, polybutylene, etc.). These "midblock" tackifying resins tend to associate with the rubbery midblock of the linear or radial block copolymer and thereby tend to extend or build up as well as tackify these rubber domains. Both natural and synthetic "essentially hydrocarbon resins" can be used as "midblock resins", provided that these resins contain at least some aliphatic character, which character can be provided by the aliphatic portion of rosin acids, repeating isoprene or other diene units (e.g. polymerized 1,3-pentadiene), polymerized cycloaliphatics, and the like.

Although esters of polyhydric alcohols and rosin acids will associate with a rubbery midblock, some of these esters tend to detract from the elastic recovery characteristics of the hot melt PSA and are not preferred. It is generally more preferable to use "essentially hydrocarbon resins", particularly the so-called "terpene" resins, i.e. polymers with repeating $C_5H_8$ or $C_{10}H_{16}$ units. These polymers can be natural or synthetic and can be copolymers (including terpolymers, etc.), since isoprene is an olefin which can be copolymerized with other olefins. Terpene-phenols have also been produced.

All terpene resins do not work with equal effectiveness in this invention, and synthetic terpenes having a softening point (ball and ring method) of about 80° to about 115° C. are preferred, particularly the commercially available resin known as "WINGTACK" 95. This commercially available terpene resin is reported to be derived from a mixed olefin feedstock as a by-product of isoprene or polyisoprene production. According to U.S. Pat. No. 3,935,338 and South African Pat. No. 700,881, "WINGTACK" 95 (trademark of Goodyear Tire and Rubber Company) is a thermoplastic tackifying resin essentially comprising a copolymer of piperylene and 2-methyl-2-butene which results from the cationic polymerization of 60% piperylene, 10% isoprene, 5% cyclopentadiene, 15% 2-methyl-butene, and about 10% dimer. Other tackifying resins of the same general type typically comprise 20-80 weight-% of piperylene and 80-20 weight-% of 2-methyl-butene.

Good elastic memory or elastic recovery characteristics can be obtained with natural hydrocarbon resins such as "PICCOLYTE D-135" (trademark), a natural dipentene terpene resin. However, this resin is not as effective as the "WINGTACK" 95 in providing good adhesive properties, e.g. good PSTC-1 peel.

The naturally occurring terpenes can be classified as monocyclic (dipentene), dicyclic (pinene), or acyclic (micrene). A small amount of cyclic character is not detrimental in the context of this invention. A significant amount of aromatic character in the terpene resin is, however, ordinarily avoided, if such aromatic character is sufficient to interfere with the midblock association properties of the resin.

As explained in British Pat. No. 1,405,786, resins with aromatic character tend to associate with the vinyl arene end blocks. Such "end block" resins include the coumarone-indenes, polystyrene, the polymethylstyrenes, the polyindenes, and other resins containing mono or polycyclic aromatic groups. Such resins are commercially available, e.g. as "PICCOTEX 75" (low molecular weight alpha-methylstyrene-vinyl toluene synthetic copolymer), "PICCOTEX 100" (trademark for higher molecular weight version of "PICCOTEX 75"), "PICCOLASTIC D-150" (trademark for polystyrene resin), and the "CUMAR" resins (trademark for coumarone-indenes). It is particularly desirable that the "end block" resin have a glass transition temperature and a softening point above those of the end block and of the "midblock" resin. For example, it would ordinarily not be desirable for the glass transition and for significant heat softening to occur in the 80°-110° C. range; hence, "end block" resins with somewhat higher molecular weights and softening points above 115° C. are typically selected. From the standpoint of strong elastic recovery (both initial and aged) and good adhesive properties, the high softening point coumarone-indene and vinyl arene (e.g. poly-alpha-methylstyrene) resins appear to be by far the most effective. Such resins with softening points within the range of 140°-160° C. are commercially available.

Considerable skill and knowledge already exist in the PSA art with respect to determining proportions of tackifiers and rubbery block copolymers. However, it has been found that these proportions cannot be selected with blind reliance upon prior experience. Nor can one rely too heavily upon PSTC-1 or probe tack values. Probe tack values and initial (immediate) PSTC-1 values hvae been found to be unreliable or unreproducible indicators of performance in the context of this invention, whereas PSTC-1 values taken 24 hours after the adhesive bond has been formed are relatively reliable and reproducible. "Dead load deformation" ("creep") and the rheological properties (G', G", loss tanget, J', and J") described previously have also been found to be reliable, reproducible parameters of PSA and elastomeric behavior.

Preferred PSTC-1 values determined 24 hours after formation of the PSA bond at room temperature on the standard steel plate using pressure from the standard 2 Kg roller include values in excess of 1 pound per inch width (1 p.i.w.), i.e. more than 450 grams 180° peel force is required to delaminate a tape/steel plate sample wherein the tape sample is 25.4 mm in width. PSTC-1 values in excess of 1500 g/25.4 mm-sample or even 3000 g/25.4 mm-sample can be obtained in practice. These values are believed to indicate a reasonably permanent or semi-permanent bond between a band of PSA and a polymeric film substrate of the type used in disposable diapers.

Tensile strength values for the PSA at 20°-25° C. can be determined as a measure of cohesive strength. Values in excess of 300 kPa (e.g. above 330 kPa) can be obtained in practice. "Dead load deformation" values (1500 g/cm$^2$ for 3 hours at the test temperature) can be well below 100% and even below 50%

$$\left( \frac{L_2 - L_1}{L_1} \times 100\% \right)$$

throughout the range of 25° C. to 50° C. It is particularly desirable that this deformation remain roughly constant over this temperature range and preferably show a gain of less than 50% (e.g. less than about 35%) at 49° or 50° C., as compared to the room temperature value.

Preferred and optimum rheological parameters are set forth below.

TABLE OF PREFERRED AND
OPTIMUM RHEOLOGICAL PROPERTIES
(All values in 10$^4$ dynes/cm$^2$ for G" and G'
and in 10$^{-8}$ cm$^2$/dyne for J' and J")

| Property | PREFERRED (at 25-50° C.) | | OPTIMUM (at 25-50° C.) | |
| --- | --- | --- | --- | --- |
| | at 0.01 Hz | at 0.25 Hz | at 0.01 Hz | at 0.25 Hz |
| Loss Modulus (G") | 4-25 | 5-50 | 5-20 | 7-25 |
| Storage Modulus (G') | 75-200 | 85-200 | 75-150 | 85-150 |
| Loss Tangent (tan δ) | .03-0.3 | .05-0.3 | .05-0.2 | .07-.25 |
| Storage Compliance (J') | 40-135 | 40-110 | 60-120 | 50-100 |
| Loss Compliance (J") | 2-20 | 5-40 | 5-15 | 5-15 |

The temperature-dependence of these values over the 25°-50° C. range is preferably minor, as indicated below.

TABLE OF BROAD AND PREFERRED LIMITS
ON VARIATIONS IN RHEOLOGICAL PROPERTIES
(All values in 10$^4$ dynes/cm$^2$, etc.
over the 25-50° C. range)

| Property | Broad Limits | | Preferred Limits | |
| --- | --- | --- | --- | --- |
| | 0.25 Hz | 0.01 Hz | 0.25 Hz | 0.01 Hz |
| G" (10$^4$ dynes/cm$^2$) | ±70 | ±10 | ±25 | ±10 |
| G' (10$^4$ dynes/cm$^2$) | ±40 | ±15 | ±25 | ±8 |
| Loss tangent | ±0.2 | ±0.2 | ±0.2 | ±0.15 |

Actual test data indicate that an "ideal" viscoelastic PSA, within the context of this invention, would have the following properties:

| | 0.01 Hz | 0.25 Hz |
| --- | --- | --- |
| G" (dynes/cm$^2$) | 1.1 × 10$^5$ | 3 × 10$^5$ |

-continued

|  | 0.01 Hz | 0.25 Hz |
| --- | --- | --- |
| G' (dynes/cm$^2$) | $1.3 \times 10^6$ | $1.75 \times 10^6$ |
| Loss tangent | 0.085 | 0.2 |
| J' (cm$^2$/dyne) | $7.7 \times 10^{-7}$ | $6 \times 10^{-7}$ |
| J" (cm$^2$/dyne) | $6 \times 10^{-8}$ | $1 \times 10^{-7}$ |

With these physical properties in mind, proportions of rubbery block copolymer and end block and midblock resins can be selected to provide an effective PSA with good elastic recovery or elastic memory characteristics. The following Table of broad, preferred, and optimum proportions assumes that the rubbery block copolymer is either (1) "SOLPRENE ® 418", trademark of Phillips Chemical Company for a radial isoprene-styrene block copolymer having an approximate molecular weight of 300,000, a specific gravity of 0.92, an inherent viscosity in toluene of 1.16, and an isoprene/styrene ratio of 85/15, or (2) KRATON ® 1111, trademark of Shell Chemical Co. for a polystyrene-polyisoprene-polystyrene (S-I-S) block copolymer containing 21.5% styrene, the balance being isoprene. This copolymer has the previously reported tensile strength, 300% modulus, elongation at break, set at break, and Shore A hardness. The Brookfield viscosity in toluene is 1300 cps.

The rubbery block copolymer preferred for PSA's of this invention is KRATON ® 1111, trademark of Shell Chemical Co. for a polystyrene-polyisoprene-polystyrene (S-I-S) block copolymer containing 21.5% styrene, the balance being isoprene. Hydrogenated linear block copolymers, including those of the styrene-isoprene-styrene type are available according to U.S. Pat. No. 3,827,999; see also U.S. Pat. No. 4,089,824, which discloses the hydrogenated butadiene analog. Such hydrogenated block copolymers can be used in the context of this invention. Compounds of the "KRATON ® G" series (trademark of Shell Chemical Company) have a saturated or essentially saturated ethylene-butylene midblock and, if used, are preferably used in combination with the KRATON ® 1111 type of rubbery block copolymer.

The aforementioned Table of proportions is set forth below.

TABLE OF PROPORTIONS FOR
BLOCK COPOLYMER AND RESINS USING HIGH BLOCK
COPOLYMER LEVELS AND MINIMAL
END BLOCK RESIN

| | Amount | | | |
| --- | --- | --- | --- | --- |
| | Preferred | | Optimum | |
| Ingredient | wt % | phr | wt % | phr |
| High styrene rubbery block copolymer | 45–75 | (100) | 51–70 | (100) |
| Midblock resin | 25–50 | 30–115 | 30–49 | 45–95 |
| End block resin | 0–9 | 0–20 | 2–7 | 3–10 |

NOTE:
phr = parts per hundred by weight, based on 100 parts block copolymer.
wt % = percentage by weight of total hot melt PSA composition.

The foregoing formulas preferably contain antioxidant, e.g. in an effective amount ranging up to 3 or 4% by weight of the PSA composition, amounts in excess of about 0.05 wt-% being typical.

The most effective criteria for the selection of amounts and types of ingredients are believed to be (a) rheological properties such as G', G", loss tangent, J' and J", and (b) dead load creep test results. It is preferred that both criteria (a) and (b) be satisfied, since there can be cases of PSA formulas which will meet one criterion but not the other. New resins and new block copolymers are constantly being discovered, and the formulation of suitable PSA's can be attempted with new materials by referring to these criteria.

It will be understood that variations in the aforementioned methods and proportions can be made without departing from the spirit and scope of this invention. For example, if the substrate to be elastic banded is heat resistant, the extruded band need not be cooled very much below its softening point and can be applied directly to the substrate while still relatively hot. However, even for such temperature resistant substrates, maintaining the extruded band at or above its softening point is neither necessary nor desirable. In another variation of the method, the extruded band need not be applied as a line or linear bead, but can be "indexed" with a moving web to provide a series of discrete circular or eliptical bands. Such "indexed" bands can provide a hat-banding effect (e.g. for mass-produced surgical caps), a gathered, banded opening for a plastic bag, a waist band, or the like. In the case of disposable diapers, however, it is not necessary for the band to form a complete circle; the essential equivalent of a circular leg band results when the diaper is pinned or snapped together at the child's hips.

The following non-limiting Examples illustrate the preferred practice of this invention. In these Examples, all parts and percentages are by weight unless otherwise indicated. The following raw materials were used in formulating the hot melt PSA's of the Examples:

"SOLPRENE ® 418": trademark for the radial block copolymer described previously.

"SOLPRENE ® 423": another trademark for essentially the same radial block copolymer in a pellet form.

"KRATON ® 1111": trademark of Shell Chemical Co. for the polystyrene-polyisprene-polystyrene copolymer described previously.

"KRATON ® 1107": trademark of Shell Chemical Co. for polystyrene-polyisoprene-polystyrene linear block copolymer having a styrene/isoprene ratio of 14/86.

"WINGTACK 95:" trademark for synthetic polyterpene resin described previously.

"WINGTACK PLUS": trademark for a synthetic polyterpene resin very similar to "WINGTACK 95" except for a minor amount of styrene units introduced to make the resin slightly more aromatic.

"KRYSTALEX ® 3100" trademark of Hercules Inc. for low molecular weight thermoplastic hydrocarbon resin of the alpha-methylstyrene type having a ring and ball softening point of 97°–103° C., an acid number less than 1.0, a bromine number which is typically about 2, a specific gravity at 25° C. of 1.06, and a melt viscosity of 10,000 centipoise (cps) at 128° C., 1,000 cps at 152° C., and 100 cps at 190° C. The softening point substantially below 115° C. (typically not more than 103° C.) indicates a spectrum of molecular weights, with a significant number of resin molecules having molecular weights well below those of the relatively pure, narrow-spectrum coumarone-indene resins which are commercially available, e.g. as the "CUMAR" (trademark) series described subsequently. (It has been found that the higher molecular weight, higher softening point, narrow-spectrum aromatic hydrocarbon resins are preferred for use as "endblock" association with the rubbery block copolymers described previously.)

"CUMAR LX-509": trademark of Neville Chemical Company for coumarone-indene resin having a softening point (by the ring and ball technique of A.S.T.M. E-28) of at least about 155° C., a specific gravity at 25/15.6° C. of 1.114, and an average molecular weight (by osmometry) of 1,120.

"EASTMAN ® Resin H-100": trademark of Eastman Kodak Company for a hydrocarbon resin produced from petroleum feedstock by polymerization, followed by hydrogenation. This particular hydrocarbon resin has an acid number less than 0.1, a density at 23° C. of 1.04 g/cm$^3$, a Brookfield viscosity at 190° C. of 200 centipoise, a bromine number of 11.1, and a ring and ball softening point (A.S.T.M. E-28) which is reported to be 100° C. and in any event is below 115° C.

"IRGANOX 1010": trademark of Ciba-Geigy for an antioxidant and thermostabilizer of the hindered phenol type.

"SOLPRENE ® 420": trademark for a branched, teleblock copolymer having polystyrene terminal blocks and a structure essentially similar to "SOLPRENE ® 423", except for a lower molecular weight.

"KRATON ® 1102": trademark for S-B-S (styrene-butadiene-styrene) block copolymer having a styrene/butadiene ratio of 28/72, a Brookfield viscosity in toluene solution (25 weight-%) of 1200 centipoise at 25° C., a specific gravity of 0.94, a Shore A hardness of 62, a set at break of 10%, an elongation of 880% (A.S.T.M. method D412 with a tensile tester jaw separation speed of 25.4 cm/min.), a 300% modulus of 281,200 Kg/m$^2$, and a tensile strength (same A.S.T.M. method as the elongation determination) of $3.23 \times 10^6$ Kg/m$^2$ determined on typical films cast from a toluene solution.

"WESTON ® 618": trademark of Borg Warner Corporation for an antioxidant described in U.S. Pat. Nos. 3,047,608 and 3,205,269, i.e. an antioxidant which is reported to be di(stearyl) pentaerythritol diphosphite.

For convenience of sample preparation, the antioxidants and pigments were sometimes omitted from the exemplary formulations which follow. Since incompatibility between resins and various portions of the rubbery block copolymer tend to be minimized in the molten state, the order of addition of ingredients is not usually critical. It is generally preferred to begin with one of the relatively larger components such as the rubbery block copolymer and add the tackifiers and other resins to it, e.g. adding the synthetic terpene "midblock" resin next, followed by the "endblock" resin. Samples can be prepared by blending in a solvent medium; however, the data obtained from such samples is believed to be less reliable as compared to samples formulated in the molten state. Samples can be solvent-cast to films ranging from 100 to 200 micrometers for test purposes, even though the industrial practice of this invention involves extrusion of the hot melt PSA.

COMPARATIVE EXAMPLE A

The following ingredients were blended in a heated mixer in the indicated amounts.

| Wt. % | Ingredient |
|---|---|
| 65.4 | Radial isoprene-styrene elastomeric block copolymer (SOLPRENE ® 423). |
| 32.7 | High softening-point, high molecular weight coumarone-indene resin (CUMAR ® LX-509). |
| 0.2 | Phosphite ester antioxidant (WESTON ® 618). |
| 0.2 | Hindered phenol antioxidant ("IRGANOX" 1010). |
| 1.5 | Titanium dioxide pigment (rutile, alumina-treated). |

A purpose of this Example was to evaluate the effect upon rheology and room-temperature 180° peel strength when the radial block copolymer/resin blend was provided with large crystalline (vinyl arene) domains and minimally tackified or plasticized rubbery (elastomeric) domains, in this case no "midblock" resin. According to the scientific and patent literature, the coumarone-indene resin probably became associated with the polystyrene end blocks of the radial elastomeric block copolymer.

COMPARATIVE EXAMPLE B

The following formula is a rubbery block copolymer/tackifier resin blend which would have low tack and peel and would have significant elastomeric behavior at normal ambient temperatures. The formula theoretically contains no "endblock" resin.

| Wt. % | Ingredient |
|---|---|
| 50 | Linear S—B—S (polystyrene-polybutadiene-polystyrene) elastomeric block copolymer (KRATON ® 1102). |
| 35 | Hydrocarbon resin (EASTMAN ® Resin H-100). |
| 15 | Staybelite Ester 10 (HERCULES ® glycerol ester of hydrogenated rosin, 83° C. softening point). |

COMPARATIVE EXAMPLE C

This formula was similar to that of Example B, except that an S-I-(polystyrene-polyisoprene-) radial block copolymer was blended with a different tackifier.

| Wt % | Ingredient |
|---|---|
| 50 | Radial S—I—elastomeric block copolymer (SOLPRENE ® 418). |
| 50 | Polyterpene resin (WINGTACK ® 95). |

COMPARATIVE EXAMPLE D

This formula had both "endblock" resin and "midblock" resin in addition to the S-I-S block copolymer; however, more than 80% by weight of the "endblock" resin was a relatively low molecular weight, low softening point material. The block copolymer was also a relatively lower molecular weight material. Room temperature performance of the formula would be expected to include poor PSA properties and some elastomeric behavior, but at higher temperatures (e.g. 37° C.), performance would be unpredictable.

| Wt. % | Ingredient |
|---|---|
| 40.0 | Low molecular weight, radial, elastomeric block copolymer (SOLPRENE ® 420). |
| 0.1 | Phosphite ester antioxidant (WESTON ® 618). |
| 0.1 | Hindered phenol antioxidant (IRGANOX" 1010). |
| 1.0 | Titanium dioxide pigment (rutile, alumina-treated). |
| 32.8 | Hydrocarbon resin (EASTMAN ® Resin H-100). |
| 4.0 | High molecular weight coumarone-indene (CUMAR ® LX-509). |
| 22.0 | Alpha-methylstyrene resin (typical softening point: 100° C.) ("KRYSTALEX" 3100 [trademark]). |

COMPARATIVE EXAMPLE E

This formula appeared to conform to all of the criteria of a formula of this invention, except that the amount of "endblock" resin was relatively high and the amount of polyterpene tackifier was relatively low.

| Wt. % | Ingredient |
|---|---|
| 45.0 | High molecular weight, radial S—I— elastomeric block copolymer (SOLPRENE ® 418). |
| 15.0 | Polyterpene resin (WINGTACK ® 95). |
| 40.0 | High molecular weight, high softening point coumarone-indene (CUMAR ® LX-509). |

COMPARATIVE EXAMPLE F

This formula generally meets the criteria of this invention, except that, because of the low styrene content in the block copolymer end blocks and the lack of any "endblock" resin, the overall formula is deficient in aromatic character and has less than the desired resistance to permanent deformation in the dead load creep test.

| Wt. % | Ingredient |
|---|---|
| 55.0 | S—I—S linear block copolymer having 14% styrene (KRATON ® 1107). |
| 44.0 | Synthetic polyterpene ("WINGTACK PLUS"). |
| 1.0 | Antioxidant. |

EXAMPLES 1 AND 2

The formulas for Examples 1 and 2 are set forth in the following Table.

| | Ingredients in Weight-% | | | |
|---|---|---|---|---|
| Example | S-I-S Linear Block Copolymer | Polyterpene Resin (WINGTACK ® PLUS) | Poly(alpha-methyl styrene)** | Antioxidant/Pigment |
| 1 | 55.0* | 38.0 | 5.0 | 2.0 |
| 2 | 55.0* | 44.0 | — | 1.0 |

*KRATON ® 1111, described previously.
**High softening point material similar in properties to CUMAR ® LX-509.

RHEOLOGICAL TESTING

The G", G', and loss tangent (G"/G') were determined, as described previously, at 25° and 50° C. and at 0.01 and 0.25 Hz. The results for the Comparative Examples and Examples 1 and 2 are set forth below. All G" and G' data are in $10^4$ dynes/cm$^2$. For purposes of comparison, typical data for natural rubber (at 0.25 Hz) are included in Table II.

TABLE I

Rheological Testing
Frequency: 0.01 Hz
Temperature: 25° C. and 50° C.

| | G" | | G' | | loss tan | |
|---|---|---|---|---|---|---|
| Example | 25° | 50° | 25° | 50° | 25° | 50° |
| A | 121 | 140 | 89.5 | 323 | 1.351 | .428 |
| B | 16.6 | 21.7 | 129 | 74.5 | .129 | .290 |
| C | 4.65 | 6.16 | 67.4 | 71.7 | .069 | .086 |
| D | 53.3 | 22.7 | 173 | 65.3 | .308 | .408 |
| E | 20.2 | 21.9 | 345 | 336 | .058 | 0.65 |
| F | 6.4 | 7.5 | 84 | 78 | .08 | .09 |
| 1 | 9.5 | 5.8 | 100 | 94 | .09 | .06 |
| 2 | 6.7 | 4.2 | 81.6 | 80.1 | .08 | 0.05 |

TABLE II

Rheological Testing
Frequency: 0.25 Hz
Temperature: 25° C. and 50° C.

| | G" | | G' | | loss tan | |
|---|---|---|---|---|---|---|
| Example | 25° | 50° | 25° | 50° | 25° | 50° |
| A | 180 | 173 | 148 | 323 | 1.215 | .440 |
| B | 31.5 | 19.3 | 171 | 110 | .187 | .173 |
| C | 15.0 | 5.48 | 78.9 | 82.3 | .190 | .067 |
| D | 138 | 45.7 | 311 | 130 | .442 | .351 |
| E | 34.3 | 23.0 | 386 | 372 | .089 | .062 |
| F | 12 | 7.8 | 100 | 92 | .12 | .08 |
| 1 | 19 | 11 | 120 | 110 | .15 | .10 |
| 2 | 14.5 | 7.9 | 101 | 91.2 | .14 | .09 |
| Natural rubber (estimated) | 40 | 40 | 800 | 800 | .05 | .05 |

For Example A, the high G' values and the temperature dependency of these values indicate unsuitability, according to the principles of this invention. The high G' may, it is believed, indicate good elastic behavior, but, conversely, poor PSA performance. The rheological parameters were confirmed by 180° peel data (PSTC-1). Even 24 hours after formation of the PSA bond, no PSTC-1 value could be obtained. "Dead load deformation" values were acceptable, ranging from 0% to only 6% throughout the 25°-50° C. range.

For Example B, the temperature dependence of G' also indicates unsuitability, which was reflected in the "dead load deformation" data. These data were as follows: 20% at room temperature, 344% at 37.8° C., and 528% at 43.3° C. Cohesive failure occurred at 48.9° C.

For example, C, G' data at 0.01 Hz were considered to be too low in the context of this invention. This analysis of the rheological parameters was confirmed by "dead load deformation" data: 6% at room temperature, 44% at 37.8° C., 92% at 43.3° C., and cohesive failure at 48.9° C. The PSTC-1 values after 24 hours were acceptable (2770 g/25.4 mm-width), indicating the ability to wet out a substrate (but inadequate resistance to heat set).

Example D had poor PSA behavior, and performed poorly in the "dead load deformation" test. It is believed that the high G" and, most important, temperature dependence of G' were significant in these regards.

The high coumarone-indene content of Example E was believed to be reflected in the high G' values. The PSA behavior of Example E was marginal (e.g. 910 g/25.4 mm-width in PSTC-1), but a sample of Example E performed adequately in the "dead load deformation" test.

Example F rheological data were generally acceptable, but samples performed poorly in the "dead load deformation" test, probably because of the relatively small vinyl arene domains.

Example 1 performed well in terms of both (1) PSTC-1 (180° peel) values taken at room temperature after 24 hours PSA bond formation (1500 g/25.4 mm-width) and (2) "dead load deformation" (16% after 3 hours at 48.9° C. and 1500 g/cm$^2$). Example 2 showed approximately the same performance as Example 1 in the "dead load deformation" test. PSTC-1 data for Example 2 are not available.

The "dead load creep" or "dead load deformation" test is a modification of A.S.T.M. D-412 (tension testing of vulcanized rubber) and the dumbbell-shaped samples were formed using Die C. See U.S. Pat. No. 4,259,220.

To provide a further standard of comparison for the rheological data obtained from Examples 1 and 2, data regarding untackified, unextended, linear A-B-A block copolymers (e.g. of the KRATON ® type) were obtained for 0.25 Hz/room temperature conditions. These data indicate that G' is typically above $300 \times 10^4$ dynes/cm$^2$ and G" is typically above $50 \times 10^4$ dynes/cm$^2$, and even, in some cases, above $100 \times 10^4$ dynes/cm$^2$. Like vulcanized natural rubber, these block copolymers exhibit excellent elastomeric behavior but, in the absence of tackifying resins, essentially no PSA behavior.

This application is a continuation-in-part of our copending application, U.S. Ser. No. 36,858, filed May 7, 1979.

What is claimed is:

1. A method for imparting elastic properties to a flexible substrate, which comprises contacting a surface of the flexible substrate with a band of a self-adhering elastic composition which consists essentially of:

a major amount by weight, not exceeding 70% by weight, of a rubbery block copolymer, which copolymer includes a rubbery midblock portion and which is terminated with vinyl arene endblocks, about 70 to 80% by weight of said rubbery block copolymer comprising said rubbery midblock portion and about 20 to about 30% by weight of said rubbery block copolymer comprising said vinyl arene endblock;

a minor amount by weight, not less than 30% by weight, of a tackifying resin generally compatible with and generally associated with said midblock portion;

2–9% by weight of an aromatic, essentially hydrocarbon resin having a glass transition temperature and a softening point above those of said vinyl arene endblocks and said tackifying resin; said aromatic, essentially hydrocarbon resin being generally compatible with and generally associated with said endblock; and 0–5% by weight of essentially inert extenders, fillers, pigments, and antioxidants that do not substantially affect the adhesive of elastic properties of the composition;

the foregoing proportions being selected to provide the following pressure-sensitive adhesive and rheological properties:
  (i) a tensile strength at 500% elongation, determined at 20°–25° C., of at least 50 pounds per square inch;
  (ii) a 180° peel resistance, according to PSTC-1, determined at 20°–25° C. for 24 hours after formation of the pressure-sensitive adhesive bond, of at least about 450 grams per 25.4 millimeter-width;
  (iii) a dead load deformation, tested at room temperature, 37.8° C., 43.3° C., and 48.9° C. for 3 hours under 1500 g/cm$^2$, of less than 50%, where dead load deformation is equal to the increased length minus the original length divided by the original length of a sample at least 25 millimeters in length, and a loss modulus, a storage, modulus, and a loss tangent measured at 0.01–0.25 Hz throughout the temperature range of 25°–50° C. as follows:
  loss modulus: $4 \times 10^4$ to $35 \times 10^4$ dynes/cm$^2$
  storage modulus: $75 \times 10^4$ to $200 \times 10^4$ dynes/cm$^2$
  loss tangent: 0.03 to 0.3.

2. The method of claim 1 wherein the flexible substrate is substantially inelastic.

3. The method of claim 2 wherein the flexible substrate is pregathered.

4. The method of claim 1 wherein prior to contacting the band with the flexible substrate the band is formed by extruding the self-adhering elastic composition at a temperature above its endblock Tg and cooling the extruded band to a temperature below its endblock Tg but above its midblock Tg.

5. The method of claim 4 wherein the band is simultaneously cooled and contacted with the flexible substrate.

6. The method of claim 1 wherein the band is placed under tension, at a temperature below its endblock Tg, in such a manner that the band is elongated when contacted with the surface of the flexible substrate and when the tension is released, gathers in the substrate form along the line of the bond between the band and the substrate.

7. The method of claim 1 wherein the band is continuously contacted with the surface of the flexible substrate.

8. The method of claim 1 wherein the flexible substrate is less than 3 millimeters thick and comprises a film of a polymeric material, a woven web or a nonwoven web.

9. The method of claim 1 wherein:
  (a) the block copolymer comprises at least one substantially amorphous midblock and at least two polyvinyl arene endblocks;
  (b) about 20 to 150 parts by weight of the midblock associating resin; and
  (c) about 10 to 150 parts by weight of the endblock associating resin which comprises an aromatic, essentially hydrocarbon endblock associating resin having a Tg and a softening point greater than the copolymer endblocks and the midblock associating resin, each per 100 parts by weight of component (a).

10. The method of claim 9 wherein the self-adhering elastic composition has the following rheological properties at a temperature of about 25°–50° C.:

|  | 0.01 Hz | 0.25 Hz |
| --- | --- | --- |
| loss modulus, $10^4$ dynes/cm$^2$ | 5–25 | 10–100 |
| storage modulus, $10^4$ dynes/cm$^2$ | 75–200 | 75–200 |
| loss tangent | 0.05–0.3 | 0.08–1.0. |

11. The method of claim 10 wherein said rheological properties are as follows:

|  | 0.01 Hz | 0.25 Hz |
| --- | --- | --- |
| loss modulus, $10^4$ dynes/cm$^2$ | 8–16 | 13–35 |
| storage modulus, $10^4$ dynes/cm$^2$ | 100–175 | 120–200 |
| loss tangent | 0.07–0.10 | 0.1–0.25. |

12. The method of claim 11 wherein the dead load deformation of said self-adhering elastic composition at 37.8° C. for 3 hours, and 1500 g/cm$^2$ of cross section, is less than about 50%.

13. An article which comprises a product of the method of claim 11.

14. The article of claim 13 which comprises a disposable diaper.

15. A method for imparting a self-adhering elastic to a flexible substrate comprising the steps of:
 (a) unreeling a band of self-adhering elastic composition from a roll, said roll being maintained at a temperature below the softening point of said self-adhering elastic and said band of self-adhering elastic being an extrudate at least 50 microns in thickness which consists essentially of (i) a block copolymer comprising at least one substantially amorphous, rubbery polymeric midblock and at least two glassy poly(vinylarene) endblocks; (ii) 30–115 parts per hundred of a midblock associating resin; and (iii) 3–20 parts per hundred of an aromatic, essentially hydrocarbon endblock associating resin having a Tg and a softening point above 115° C. each per one hundred parts of the block copolymer; wherein the proportions (i), (ii), and (iii) are selected to provide the following properties:
  (i) a tensile strength at 500% elongation, determined at 20°–25° C., of at least 50 pounds per square inch;
  (ii) a 180° peel resistance, according to PSTC-1, determined at 20°–25° C. 24 hours after formation of the pressure-sensitive adhesive bond, of at least about 450 grams per 25.4 mm-width;
  (iii) a dead load deformation, tested at 37.8° C. and 1500 g/cm$^2$, less than 50%; and
  (iv) a loss modulus of $5 \times 10^4$ to $100 \times 10^4$ dynes/cm$^2$, a storage modulus of $65 \times 10^4$ to $225 \times 10^4$ dynes/cm$^2$, and a loss tangent of 0.3 to 1.0, at 0.01–0.25 Hz at 25°–50° C.;
 (b) contacting the band of self-adhering elastic with a surface of a flexible substrate forming a bond between the substrate and elastic.

16. The method of claim 15 wherein the substrate is substantially inelastic.

17. The method of claim 15 wherein the band is placed under tension in such a manner that it is elongated when contacted with the flexible substrate and when the tension is released, gathers in the substrate form along the line of the bond between the band and the substrate.

18. The method of claim 15 wherein the band has a backing.

19. The method of claim 18, wherein the backing of the band comprises a release liner which is removed from the band prior to contacting the band with the flexible substrate.

20. The method of claim 18, wherein the backing of the band is substantially elastomeric.

21. The method of claim 18 wherein the self-adhering elastic has been formed by coextruding the backing and the band, and wherein the backing has release characteristics.

22. An article which comprises a product of the method of claim 15.

23. The article of claim 22 which comprises a disposable diaper.

* * * * *

UNITED STATES PATENT AND TRADEMARK OFFICE
CERTIFICATE OF CORRECTION

PATENT NO. : 4,543,099

DATED : September 24, 1985

INVENTOR(S) : WILLIAM L. BUNNELLE and RICHARD C. LINDMARK, Jr.

It is certified that error appears in the above-identified patent and that said Letters Patent is hereby corrected as shown below:

On the title page:
  In Item [62], please add --,which is a continuation-in-part of Ser. No. 141,959, April 21, 1980, now abandoned; which was a divisional of Ser. No. 36,858, May 7, 1979, now U.S. Pat. No. 4,259,220; which was a continuation-in-part of Ser. No. 944,845, September 22, 1978, now abandoned, and Ser. No. 966,794, December 6, 1978, now abandoned; which was a continuation-in-part of Ser. No. 944,845, September 22, 1978, now abandoned.--

In the Abstract", at line 6, for "in to" read --into--.
Column 3, line 66, for "fo" read --of--.
Column 5, line 7, for "modulus (G')," read --"modulus" (G'),--.
Column 5, line 7, for "compliance (J")" read --"compliance" (J")--.
Column 10, line 2, for "and blocks" read --end blocks--.
Column 17, line 66, for "tangient" read --tangent--.
Column 20, line 22, for "storage, modulus" read --storage modulus--.
Column 21, line 25, for "claim 11" read --claim 1--.

Signed and Sealed this

Twenty-first Day of January 1986

[SEAL]

Attest:

DONALD J. QUIGG

Attesting Officer    Commissioner of Patents and Trademarks